United States Patent
Star-Lack et al.

(10) Patent No.: US 10,390,787 B2
(45) Date of Patent: Aug. 27, 2019

(54) OPTIMIZATION OF IMAGE ACQUISITION PARAMETERS FOR REGISTRATION WITH REFERENCE IMAGE

(71) Applicant: Varian Medical Systems, Inc., Palo Alto, CA (US)

(72) Inventors: Josh M. Star-Lack, Palo Alto, CA (US); Michelle M. Svatos, Oakland, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 15/277,562

(22) Filed: Sep. 27, 2016

(65) Prior Publication Data
US 2018/0085083 A1   Mar. 29, 2018

(51) Int. Cl.
*A61B 6/03* (2006.01)
*A61B 6/00* (2006.01)
(Continued)

(52) U.S. Cl.
CPC .............. *A61B 6/542* (2013.01); *A61B 6/032* (2013.01); *A61B 6/4085* (2013.01); *A61B 6/488* (2013.01); *G06T 7/30* (2017.01); *G06T 11/003* (2013.01); *A61N 5/1049* (2013.01); *A61N 2005/1061* (2013.01); *G06T 2207/10081* (2013.01)

(58) Field of Classification Search
CPC .......... A61B 6/542; A61B 6/54; A61B 6/541; A61B 6/544; A61B 6/545; A61B 6/032; A61B 6/03; A61B 6/037; A61B 6/022; A61B 6/025; G06T 7/0014; G06T 7/0012; G06T 7/001; G06T 7/0002; G06T 7/00;
(Continued)

(56) References Cited

U.S. PATENT DOCUMENTS 5,717,838 A * 2/1998 LeClair ................. G06K 15/02
                                                 358/1.9
6,888,919 B2   5/2005 Graf
(Continued)

OTHER PUBLICATIONS

Wang, Adam S., et al. "Low-dose preview for patient-specific, task-specific technique selection in cone-beam CT." Medical physics 41.7 (2014).

*Primary Examiner* — Dwayne D Bost
*Assistant Examiner* — Stephen M Brinich
(74) *Attorney, Agent, or Firm* — Vista IP Law Group, LLP

(57) ABSTRACT

An apparatus includes input(s) for obtaining a first image and for obtaining a plurality of image parameters that includes at least a first image parameter and a second image parameter; a simulated image creation module configured for computing a plurality of simulated images based on the first image and the plurality of image parameters, the plurality of simulated images having at least a first simulated image computed based on the first image parameter, and a second simulated image computed based on the second image parameter, wherein the first simulated image has a first image quality, the second simulated image has a second image quality, and the first image quality is different from the second image quality; an image registration module configured for performing a plurality of image registrations using the simulated images; and a non-transitory medium configured for storing results from the act of performing the plurality of image registrations.

43 Claims, 5 Drawing Sheets

(51) Int. Cl.
*G06T 11/00* (2006.01)
*G06T 7/30* (2017.01)
*A61N 5/10* (2006.01)

(58) Field of Classification Search
CPC ...... G06T 11/003; G06T 11/00; G06T 11/001;
G06T 11/005; G06T 11/008
USPC ........ 382/128, 130–131, 154, 162–169, 216,
382/206; 358/448, 461, 518–523
See application file for complete search history.

(56) References Cited

U.S. PATENT DOCUMENTS

| | | |
|---|---|---|
| 7,649,981 B2 | 1/2010 | Seppi et al. |
| 2001/0006425 A1* | 7/2001 | Takamori ................ H04N 1/40 |
| | | 358/530 |
| 2007/0286332 A1* | 12/2007 | Gohno ................... A61B 6/032 |
| | | 378/15 |
| 2009/0080719 A1* | 3/2009 | Watt ...................... G06F 3/1446 |
| | | 382/128 |

* cited by examiner

OPTIMIZATION OF IMAGE ACQUISITION PARAMETERS FOR REGISTRATION WITH REFERENCE IMAGE

FIELD

This application relates generally to medical imaging, and more particularly, to systems and methods for determining image acquisition parameters for image registration.

BACKGROUND

Radiotherapy has been used in the treatment of tumors, such as tumors in lung, abdomen, head, etc. In radiation therapy, it is important to take an image of the patient in the treatment position immediately prior to delivering treatment beam. This image is used to fine tune the patient alignment by comparing it to a reference (e.g., planning) CT image, and by performing a registration (e.g., image matching) in order to determine if the patient position or pose needs to be modified before the radiation treatment beam is delivered. The image for the registration is not intended for medical diagnostic purpose, and therefore the image quality does not require extraordinarily fine detail. Rather, the goal is to have just enough x-ray dose so that anatomical landmarks are visible for guiding the registration. Any additional x-ray dose that is beyond that required will be causing unnecessary exposure risk to the patient. In some cases, a treatment course may be divided into multiple (e.g., thirty or more) daily sessions, which each session requiring at least one image for registration. Accordingly, it may be desirable to lower a dose level associated with the acquisition of image for registration purpose.

In some cases, it may also be desirable to optimize the image acquisition so that only the needed gantry or projection angles are used. A CBCT image set may be reconstructed from projections ranging over 200 to 360 degrees with angular spacing of approximately 0.5 degrees. However, it is not clear if so much angular information is required for the registration. Digital tomosynthesis (DTS) is a type of imaging in which the angular span of the images is reduced. An advantage of DTS imaging is that it uses less x-ray dose (since there are fewer projections) and less time for data acquisition (since there are fewer projections and the gantry does not have to travel as far). However, a difficulty with DTS imaging is that it may be difficult to know a priori what the optimal vergence angle should be, and where the acquisition should be centered.

Apparatus and methods for determining image acquisition parameters for image registration are described herein.

SUMMARY

An apparatus includes one or more input for obtaining a first image and for obtaining a plurality of image parameters that includes at least a first image parameter and a second image parameter; a simulated image creation module configured for computing a plurality of simulated images based on the first image and the plurality of image parameters, the plurality of simulated images having at least a first simulated image computed based on the first image parameter, and a second simulated image computed based on the second image parameter, wherein the first simulated image has a first image quality, the second simulated image has a second image quality, and the first image quality is different from the second image quality; an image registration module configured for performing a plurality of image registrations using the simulated images; and a non-transitory medium configured for storing results from the act of performing the plurality of image registrations.

Optionally, the first image comprises a CT image.

Optionally, the first image parameter corresponds with a first dose, and the second image parameter corresponds with a second dose that is different from the first dose.

Optionally, the first image parameter corresponds with a first current value for image acquisition, and the second image parameter corresponds with a second current value that is different from the first current value. In some cases, the first current value may be a value of a current that is in an imaging component for obtaining an image.

Optionally, the first image parameter corresponds with a first period for image acquisition, and the second image parameter corresponds with a second period that is different from the first period. In some cases, the first period may be a duration for application of dose to obtain an image.

Optionally, the first image parameter corresponds with a first number of projection images, and the second image parameter corresponds with a second number of projection images that is different from the first number of projection images.

Optionally, the image registration module is configured to register the first simulated image with a reference image and to register the second simulated image with the reference image.

Optionally, the reference image comprises the first image or a portion of the first image.

Optionally, the reference image is derived from the first image.

Optionally, the image registration module is configured to provide a plurality of values representing how well the respective simulated images match with a reference image.

Optionally, the values comprise cross correlation values.

Optionally, the values comprise mutual information.

Optionally, the image registration module is configured to use a rigid registration algorithm to perform the plurality of image registrations.

Optionally, the image registration module is configured to use a deformable registration algorithm to perform the plurality of image registrations.

Optionally, the image registration module is configured to perform the plurality of image registrations based on a match criteria.

Optionally, the image registration module is configured to perform the plurality of image registrations based on an input from a user.

Optionally, the input comprises a region-of-interest.

Optionally, the input comprises an identification of a structure.

Optionally, the apparatus further includes an image acquisition parameter determination module configured for obtaining an image acquisition parameter based on at least one or more of the results.

Optionally, the image acquisition parameter corresponds with one of the simulated images that satisfies a cut-off criteria, and has a lowest corresponding dose.

Optionally, the image acquisition parameter is for obtaining a second image.

Optionally, the image acquisition parameter is for obtaining the second image during a patient setup procedure.

An image processing method includes: obtaining a first image; obtaining a plurality of image parameters that includes at least a first image parameter and a second image parameter; computing a plurality of simulated images based on the first image and the plurality of image parameters, the plurality of simulated images having at least a first simulated image computed based on the first image parameter, and a second simulated image computed based on the second image parameter, wherein the first simulated image has a first image quality, the second simulated image has a second image quality, and the first image quality is different from the second image quality; performing a plurality of image registrations using the simulated images; and storing results from the act of performing the plurality of image registrations.

Optionally, the first image comprises a CT image.

Optionally, the first image parameter corresponds with a first dose, and the second image parameter corresponds with a second dose that is different from the first dose.

Optionally, the first image parameter corresponds with a first current value for image acquisition, and the second image parameter corresponds with a second current value that is different from the first current value.

Optionally, the first image parameter corresponds with a first period for image acquisition, and the second image parameter corresponds with a second period that is different from the first period.

Optionally, the first image parameter corresponds with a first number of projection images, and the second image parameter corresponds with a second number of projection images that is different from the first number of projection images.

Optionally, the act of performing the plurality of image registrations using the simulated images comprises registering the first simulated image with a reference image and registering the second simulated image with the reference image.

Optionally, the reference image comprises the first image or a portion of the first image.

Optionally, the reference image is derived from the first image.

Optionally, the act of performing the plurality of image registrations results in a plurality of values representing how well the respective simulated images match with a reference image.

Optionally, the values comprise cross correlation values.

Optionally, the values comprise mutual information.

Optionally, the act of performing the plurality of image registrations comprises using a rigid registration algorithm.

Optionally, the act of performing the plurality of image registrations comprises using a deformable registration algorithm.

Optionally, the image processing method further includes obtaining match criteria, wherein the act of performing the plurality of image registrations is performed based on the match criteria.

Optionally, the image processing method further includes obtaining an input from a user, wherein the act of performing the plurality of image registrations is performed based on the input from the user.

Optionally, the input comprises a region-of-interest.

Optionally, the input comprises an identification of a structure.

Optionally, the image processing method further includes obtaining an image acquisition parameter that is determined based on at least one or more of the results.

Optionally, the image acquisition parameter corresponds with one of the simulated images that satisfies a cut-off criteria, and has a lowest corresponding dose.

Optionally, the image processing method further includes using the image acquisition parameter to obtain a second image.

Optionally, the second image is obtained during a patient setup procedure.

A product includes a non-transitory medium storing instructions, an execution of which causes a processing unit to perform a method, the method comprising: obtaining a first image; obtaining a plurality of image parameters that includes at least a first image parameter and a second image parameter; computing a plurality of simulated images based on the first image and the plurality of image parameters, the plurality of simulated images having at least a first simulated image computed based on the first image parameter, and a second simulated image computed based on the second image parameter, wherein the first simulated image has a first image quality, the second simulated image has a second image quality, and the first image quality is different from the second image quality; and performing a plurality of image registrations using the simulated images.

Other and further aspects and features will be evident from reading the following detailed description of the embodiments.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

DESCRIPTION OF THE EMBODIMENTS

Figure 1:
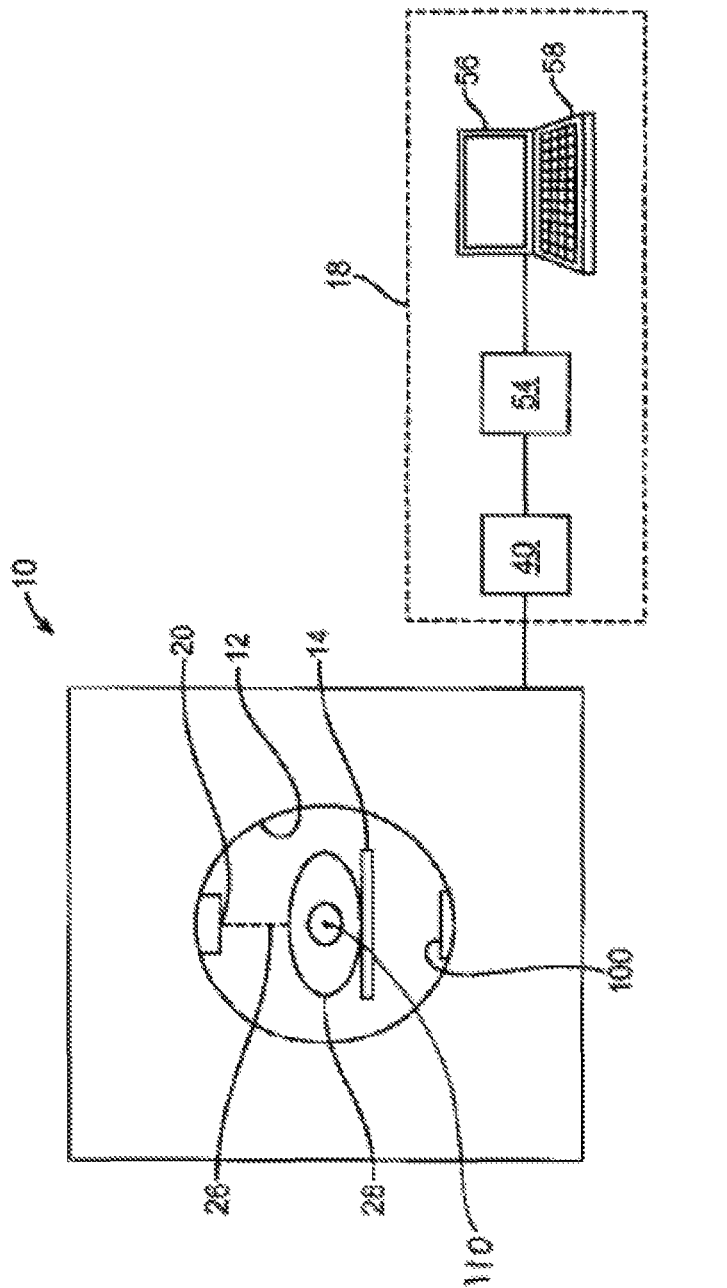
FIG. 1 illustrates a radiation system that may be used to implement one or more embodiments described herein.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 illustrates a radiation system 10 that may be used to implement one or more embodiments described herein. The system 10 includes a gantry 12, a patient support 14 for supporting a patient 28, and a control system 18 for controlling an operation of the gantry 12. The system 10 also includes a radiation source 20 that projects a beam 26 of radiation towards the patient 28 while the patient 28 is supported on support 14, and an imager 100 located at an operative position relative to the source 20 (e.g., under the support 14). The radiation source 20 can be configured to generate a cone beam (e.g., as for CBCT), a fan beam, or other types of radiation beams in different embodiments.

In the illustrated embodiments, the radiation source 20 is a diagnostic radiation source for providing diagnostic energy. In such cases, the imager 100 is configured to receive diagnostic radiation and generate image signals in response thereto. In other embodiments, in addition to being a diagnostic radiation source, the radiation source 20 is also a treatment radiation source for providing treatment energy. In such cases, the imager 100 is configured to selectively receive diagnostic radiation or treatment radiation and generate image signals in response thereto. In further embodiments, instead of being a diagnostic radiation source, the radiation source 20 is a treatment radiation source. In such cases, the imager 100 is configured to receive treatment radiation and generate image signals in response thereto. In the embodiments in which the radiation source 20 is configured to deliver treatment radiation, the system 10 may optionally further include a collimator for changing a characteristic (e.g., shape) of the radiation beam.

In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. Radiation sources capable of generating X-ray radiation at different energy levels are described in U.S. patent application Ser. No. 10/033,327, entitled "RADIOTHERAPY APPARATUS EQUIPPED WITH AN ARTICULABLE GANTRY FOR POSITIONING AN IMAGING UNIT," filed on Nov. 2, 2001, now issued as U.S. Pat. No. 6,888,919, and U.S. patent application Ser. No. 10/687,573, entitled "MULTI-ENERGY X-RAY SOURCE," filed on Oct. 15, 2003, now issued as U.S. Pat. No. 7,649,981. In the illustrated embodiments, the radiation source 20 is coupled to a ring gantry and is located within a bore. In other embodiments, the radiation source 20 may be coupled to an arm gantry.

In the illustrated embodiments, the control system 18 includes a processor 54, such as a computer processor, coupled to a control 40. The control system 18 may also include a monitor 56 for displaying data and an input device 58, such as a keyboard or a mouse, for inputting data. In the illustrated embodiments, the gantry 12 is rotatable about the patient 16, and during an imaging and/or a treatment procedure, the gantry 12 rotates about the patient 28 (as in a CT procedure and/or an arch-therapy). In other embodiments, the gantry 12 does not rotate about the patient 28 during a procedure. In such case, the gantry 12 may be fixed, and the patient support 14 is rotatable. The operation of the radiation source 20 and the gantry 12 (if the gantry 12 is rotatable) are controlled by the control 40, which provides power and timing signals to the radiation source 20, and controls a rotational speed and position of the gantry 12, based on signals received from the processor 54. Although the control 40 is shown as a separate component from the gantry 12 and the processor 54, in alternative embodiments, the control 40 can be a part of the gantry 12 or the processor 54.

It should be noted that the system 10 is not limited to the example described above, and that the system 10 may have other configurations in other embodiments. For example, in other embodiments, the system 10 may have different shapes. In other embodiments, the system 10 may have different ranges of motions and/or degrees of freedom. For example, in other embodiments, the radiation source 20 may be rotatable about the patient 28 completely through a 360° range, or partially through a range that is less than 360°. Also, in other embodiments, the radiation source 20 is translatable relative to the patient 28. In still further embodiments, the system 10 may be any imaging system that has imaging capability.

Figure 2:
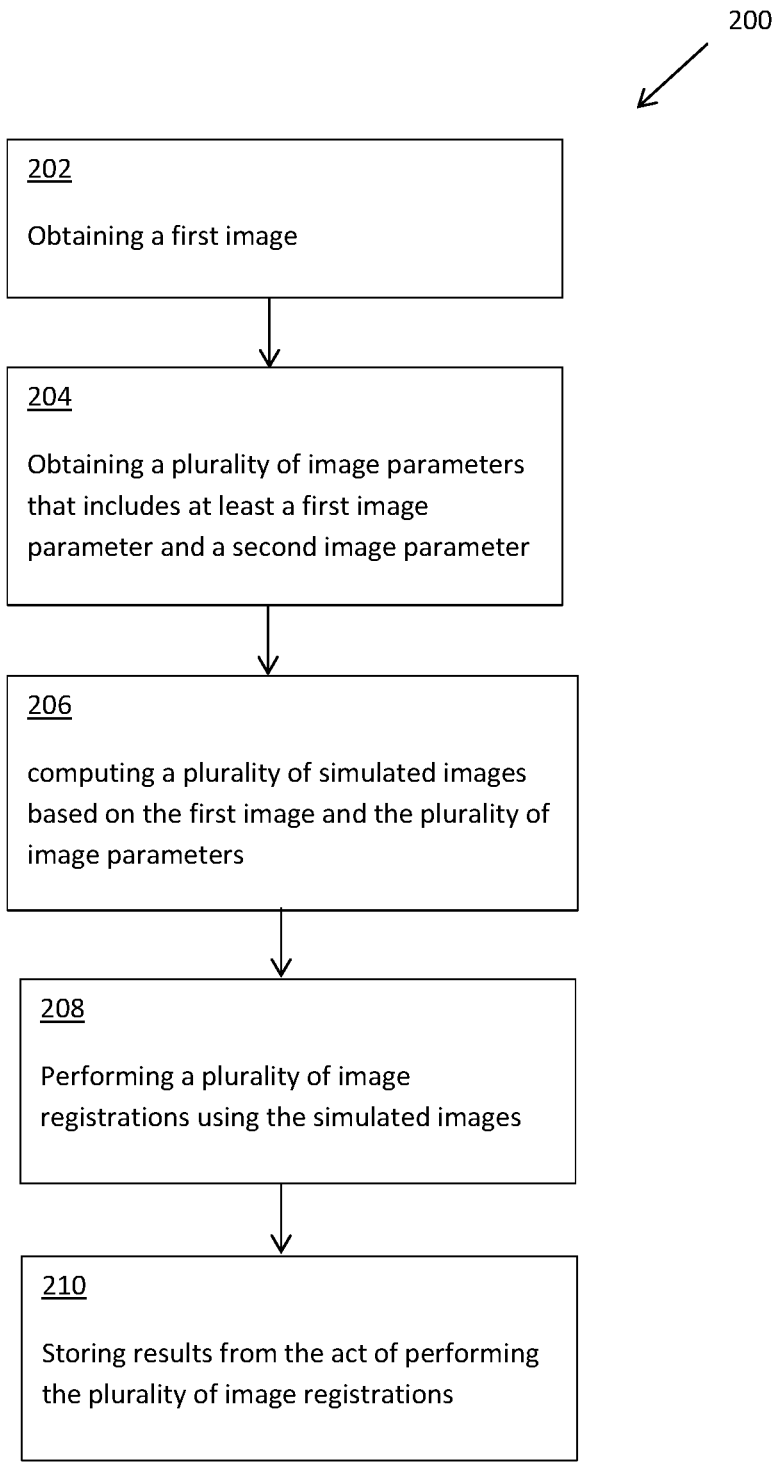
FIG. 2 is a flow diagram illustrating a method for determining image acquisition parameters.

FIG. 2 is a flow diagram illustrating a method 200 for determining image acquisition parameter(s). In some embodiments, the image acquisition parameter(s) determined from the method 200 may be used for obtaining an image for registration with a reference image during a patient setup procedure. In other embodiments, the image acquisition parameter(s) may be used for obtaining images for other purposes. In the illustrated embodiments, the method 200 is performed using the apparatus of FIG. 3, and accordingly, the method 200 will be described with reference to the apparatus of FIG. 3. However, it should be understood that the method 200 may be performed by other apparatuses in other embodiments.

Referring to the method 200 of FIG. 2, first, a first image is obtained (item 202). In some cases, the first image may be a CT image, or a part of a CT image. In other cases, the first image may be a tomosynthesis image, or a part of a tymosynthesis image. In further cases, the first image may be a projection image. The first image may be generated during a treatment planning session. Alternatively, the first image may be generated during a diagnostic imaging session. In some embodiments, item 202 may be performed by the radiation system 10 of FIG. 1, which generates the first image. Alternatively or additionally, item 202 may be performed by the apparatus 300 of FIG. 3, which receives the first image. As shown in the figure, the apparatus 300 has an input 310 configured to receive the first image. The input 310 may receive the first image that is stored in a non-transitory medium (e.g., memory, database). The non-transitory medium may be a part of the apparatus 300, or may be communicatively coupled to the apparatus, e.g., by a cable or wirelessly.

Returning to FIG. 2, next, a plurality of image parameters is obtained (item 204). In the illustrated example, the image parameters are obtained by an input 312 at the apparatus 300 shown in FIG. 3. In some cases, item 204 may be performed by the apparatus 300 that receives the image parameters. The image parameters may be retrieved from a non-transitory medium (e.g., memory, database). The non-transitory medium may be a part of the apparatus 300, or may be communicatively coupled to the apparatus, e.g., by a cable or wirelessly. In other cases, item 204 may be performed by the apparatus 300 that receives the image parameters as user input entered by a user via a user interface. For example, the apparatus may provide a user interface that allows the user to input information. By means of non-limiting examples, the user interface may include a graphical display and may allow a user to input information through a touch screen, a keyboard, a mouse, etc.

The image parameters are for use by the apparatus 300 to create multiple simulated images based on the first image. In particular, the apparatus 300 is configured to use image data associated with the first image and process such image data based on the image parameters to create multiple simulated images. Each simulated image has a certain image quality that is different from the others. For example, there may be ten image parameters P1-P10 for creating ten simulated images S1-S10, respectively. The image parameters P1-P10 are selected such that when the simulated images S1-S10 are created, each simulated image will correspond with a certain image feature or quality that is different from the others. For example, the simulated images S1-S10 may have respective image features or qualities Q1-Q10, each having an unique value. Different techniques may be employed to measure the image features or qualities. In some embodiments, the image feature or quality for each image may be obtained by determining spatial resolution (which is a measure of how well fine line pairs, or other high contrast objects, in the image can be discerned). In other embodiments, the image feature or quality may be obtained by determining contrast resolution (which is a measure of how well differences in gray scale can be distinguished). In further embodiments, the image feature or quality for each image may be obtained by determining signal-to-noise ratio for the image. In the above embodiments, a simulated image is generated based on one image parameter. In other embodiments, a simulated image may be generated based on multiple image parameters. In such cases, each of the simulated images may be generated based on a corresponding one of the sets of image parameters.

By means of non-limiting examples, the image parameters may correspond with different respective dose values, different respective current values, different respective periods (durations), different respective number of projection images, or any combination of the foregoing. Image created using lower dose will generally have a lower image quality. Thus, in some cases, the image parameters may be selected such that different simulated images corresponding with different dose values (for creating different images) can be created by the apparatus 300. Also, images created using lower current will generally have a lower image quality. Thus, the image parameters may be selected such that different simulated images corresponding with different current values (for creating different images) can be created by the apparatus 300. Furthermore, image created using shorter beam-on period (duration) may have a lower image quality. Thus, the image parameters may be selected such that different simulated images corresponding with different beam-on periods (for creating different images) can be created by the apparatus 300. In addition, image constructed using a lower number of projection images may have a lower image quality. Accordingly, the image parameters may be selected such that different simulated images corresponding with different numbers of projection images (for creating different images) can be created by the apparatus 300.

In some cases, the image parameters include at least a first image parameter and a second image parameter. In some embodiments, the first image parameter corresponds with a first dose, and the second image parameter corresponds with a second dose that is different from the first dose. In other embodiments, the first image parameter corresponds with a first current value for image acquisition, and the second image parameter corresponds with a second current value that is different from the first current value. In further embodiments, the first image parameter corresponds with a first period for image acquisition, and the second image parameter corresponds with a second period that is different from the first period. In still further embodiments, the first image parameter corresponds with a first number of projection images, and the second image parameter corresponds with a second number of projection images that is different from the first number of projection images. In other cases, the image parameters include more than two (e.g., three, four, five, etc.) image parameters.

In the illustrated embodiments, the apparatus 300 has an input 310 for obtaining the first image, and an input 312 for obtaining image parameters. In other embodiments, the input 310 and the input 312 may be implemented as a single input.

Returning to FIG. 2, next, a plurality of simulated images is computed based on the first image and the plurality of image parameters (item 206). Various techniques may be employed to create the simulated images using the first image, and using the image parameters. In some embodiments, the image parameter represents an amount of noise (e.g., random noise) to be added to an image, and the simulated image is created by adding the amount of noise to the first image. The amount of noise may correspond with a certain quantity of dose. For example, the amount of noise may be determined, such that when the noise is added to the first image, the resulting simulated image will have a certain feature or quality as though it were acquired with the quantity of dose (corresponding with the amount of noise). Thus, the simulated image will have a degrading image quality. The noise makes it harder to discern the details in the image, which may make it harder to register, or "line up", the images accurately. To make the image even worse (e.g., as if it were acquired with less dose), more noise may be added. Thus, another simulated image with a more degraded quality may be generated by introducing more noise to the first image.

In other embodiments, the image parameter may be any image degradation factor, which may be applied to an image to degrade the image in some respects.

Figure 3:
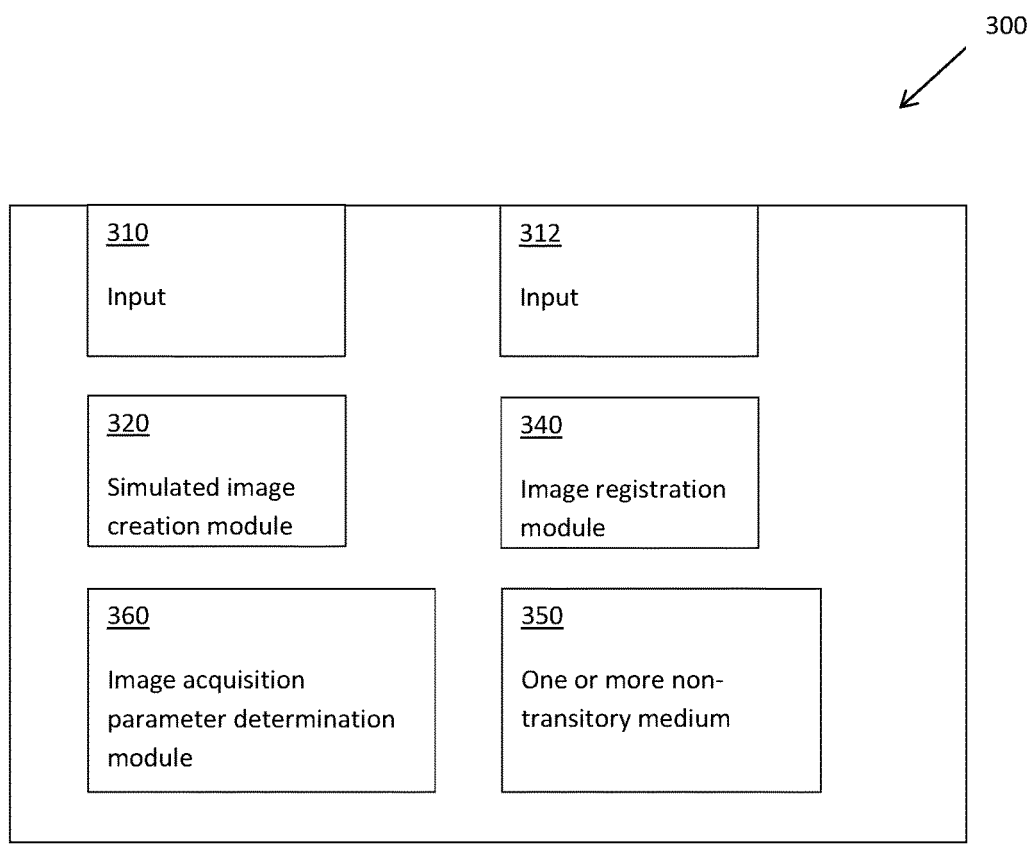
FIG. 3 illustrates an apparatus for determining image acquisition parameters.

The simulated images may be determined using a simulated image creation module 320 in the apparatus 300 (FIG. 3). The simulated image creation module 310 is configured to obtain the first image and the image parameters as inputs, and to execute an image creation algorithm to create the multiple simulated images.

As discussed, the image parameters are selected such that when the simulated images are created, each simulated image will correspond with a certain image feature or quality that is different from the others. For example, the simulated images S1-S10 may have respective image features or qualities Q1-Q10. The different image qualities may correspond with different respective different respective imaging dose values, different respective current values, different respective beam-on periods, different respective number of projection images, or any combination of the foregoing.

In some cases, the plurality of simulated images has at least a first simulated image computed based on the first image parameter, and a second simulated image computed based on the second image parameter. The first simulated image has a first image quality, the second simulated image has a second image quality, and the first image quality is different from the second image quality. The first simulated image may have a certain feature or quality that corresponds with a first dose value for imaging, and the second simulated image may have a certain feature or quality that corresponds with a second dose value for imaging that is different from the first dose. For example, the first dose may be lower than the second dose. In such cases, the first simulated image may have a higher resolution than the second simulated image because imaging using higher dose will result in image having relatively higher resolution.

In some embodiments, the created simulated images may be stored in one or more non-transitory medium 350. In the illustrated embodiments, the one or more non-transitory medium 350 is in the apparatus 300, or may be considered as a part of the apparatus 300. In other embodiments, the one or more non-transitory medium may not be a part of the apparatus 300, and may be communicatively coupled to the apparatus 300. For example, the non-transitory medium may be the one or more non-transitory medium 350 shown in FIG. 3.

Returning to FIG. 2, next, a plurality of image registrations is performed using the simulated images (item 208). In the illustrated example shown in FIG. 3, item 208 may be performed by an image registration module 340 in the apparatus 300. In particular, the image registration module 340 may be configured to register the multiple simulated images (e.g., first simulated image, second simulated image, etc.) with a reference image R. The reference image R may be the first image, or a portion of the first image. Alternatively, the reference image may be derived from the first image. In one implementation, the image registration 340 registers each of the simulated images with the reference image R by comparing (e.g., matching) each of the simulated images with the reference image R. The act of performing the plurality of image registrations results in a plurality of values representing how well the respective simulated images match with a reference image R. In some cases, the values comprise cross correlation values. In other cases, the values comprise mutual information.

In some cases, the image registration module 340 may be configured to perform the plurality of image registrations using a rigid registration algorithm. In other cases, the image registration module 340 may be configured to perform the plurality of image registrations using a deformable registration algorithm.

Different techniques may be employed to perform the registration in different embodiments. In some embodiments, the image registration may be performed automatically using the image registration module 340. For example, in some embodiments, the image registration module 340 may be configured to determine cross-correlation or mutual information. Each of these techniques involves analyzing images as arrays of pixel values, where each pixel in the image is a number representing the gray scale. The image registration module 340 repeatedly puts the image in different positions relative to the reference image, and compares the pixel values in these images. The position that results in the least difference of all the pixel values (e.g., in the image or a region of interest) will be the registered image position. In some cases, the image registration module 340 may determine a displacement vector, which represents a direction and an amount of movement the image of the patient needed in order to bring the image into alignment with the reference image.

In other embodiments, the image registration may be performed manually (e.g., by eye). For example, a user may view the two images, and may use an user interface to move one image relative to the other image, until objects in the two overlapping images are aligned.

Returning to FIG. 2, next, results from the act of performing the plurality of image registrations are stored in a non-transitory medium (item 210). The non-transitory medium may be a part of the apparatus 300, or may be communicatively coupled to the apparatus 300 (e.g., through a cable or a wireless connection). For example, the non-transitory medium may be the one or more non-transitory medium 350 shown in FIG. 3.

In some embodiments, the image processing method 200 may further include obtaining match criteria by the apparatus 300. In such cases, the act of performing the plurality of image registrations may be performed based on the match criteria. The match criteria may concern the feature of the image that is most important to align, and may be assigned a number representing how close the features in the respective images need to be. For example, the match criteria may require that a bone feature in the image be exactly on top of, or exactly aligned with, a bone feature in the reference image. In another example, the match criteria may require that a marker seed in the image be exactly aligned with the corresponding marker in the reference image. As a further example, the match criteria may prescribe how well softer tissues (which may not have clear outlines in either image) in the images need to match up. In some cases, the match will not be exact, and there will be some differences in the corresponding pairs of pixel values. In some embodiments, the match criteria may include a component for bone feature, a component for implanted marker(s), a component for soft tissues, or any combination of the foregoing. Also, in some embodiments, importance factors may be assigned for each of the categories (e.g., bone, marker, soft tissue, etc.) in the match criteria. For example, bone feature may be assigned a higher importance factor if it is determined that it is more important to match up bone features in the two images.

In addition, in some embodiments, the image processing method 200 may further include obtaining an input from a user. For example, the apparatus 300 may provide a user interface for allowing a user to enter input into the apparatus 300. In such cases, the act of performing the plurality of image registrations may be performed based on the input from the user. By means of non-limiting examples, the user input may comprise a region-of-interest, an identification of a structure in an image, one or more parameters for defining a match criteria for image registration, etc., or any combination of the foregoing. Also, in other embodiments, the user input may be an instruction to move one image relative to another image in a certain direction and by a certain amount, or any other input that may be used to perform registration manually.

In some embodiments, the image processing method 200 further includes obtaining an image acquisition parameter that is determined based on at least one or more of the results (from the registrations). Such may be accomplished using an image acquisition parameter determination module 360 in the apparatus 300 (FIG. 3).

In the illustrated embodiments, the image acquisition parameter determination module 360 may include a ranking module, which ranks results from the image registrations. In one implementation, the image registrations will result in a plurality of simulated images that satisfy a match criteria (e.g., a cut-off criteria). Among the winning simulated images (i.e., those that satisfy the match criteria), the image acquisition parameter determination module 360 then examines the acquisition parameters associated with the corresponding winning simulated images, and the ranking module then ranks the simulated images with respect to dose. In some cases, the apparatus 300 may output the ranking for display to a user, which allows the user to select one or more of the parameters associated with a winning simulated image for future image acquisition(s). Alternatively or additionally, the apparatus 300 may include a recommendation module for providing one or more recommended parameter(s) to the user for future image acquisition(s). In some cases, the recommendation module of the apparatus 300 may select the parameters that result in the least dose and/or acquisition time for future image acquisition(s). For example, it may be determined the simulated images S7-S10 satisfy the match criteria, and simulated images S1-S6 fail the match criteria. In such cases, the apparatus 300 examines simulated images S7-S10 to determine which of these images S7-S10 has a lowest corresponding dose and/or acquisition time. Assuming simulated image S8 has the lowest corresponding dose and/or acquisition time, the recommendation module of the apparatus 300 may then select the parameters (e.g., the parameters used to generate the simulated image S8, and/or parameters associated with the simulated image S8) as the recommended parameters for future image acquisition(s).

Figure 4:
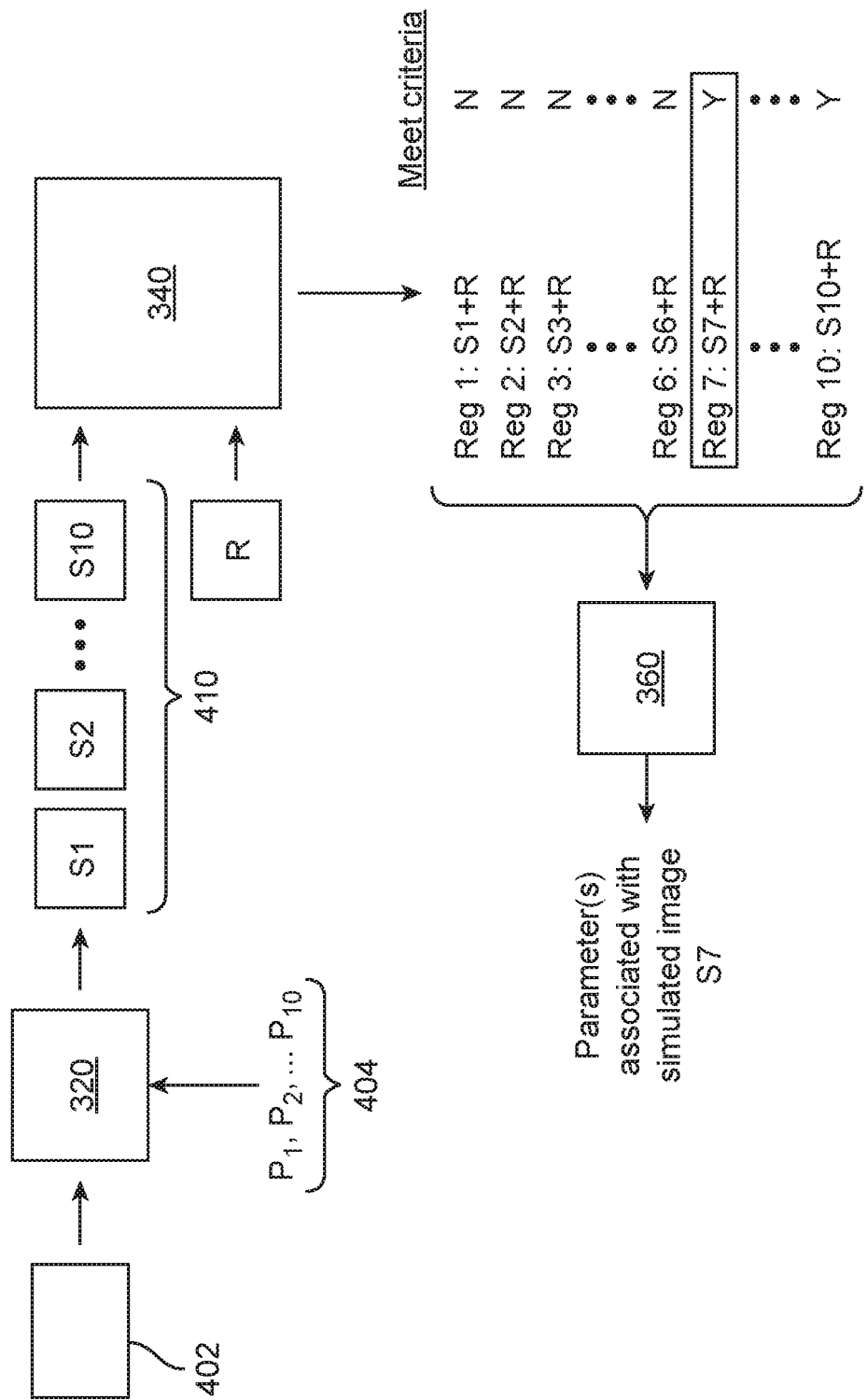
FIG. 4 illustrates a concept of the method of FIG. 2.

FIG. 4 illustrates a concept of the method of FIG. 2. As shown in FIG. 4, a first image 402 is first obtained (from item 202 in the method 200). Also, multiple image parameters 404 are obtained (from item 204 in the method 200). From the first image 402, a multiple simulated images 410 are generated based on the plurality of image parameters 404 (item 206 in the method 200). Then multiple image registrations are performed using the simulated images 410 against a reference image R (item 208). The reference image R may be the first image 402 or another image that is used as a reference image. The image registrations result may indicate that one or more of the simulated images 410 satisfy a match criteria, while other one(s) of the simulated images 410 may fail the match criteria. The simulated image that satisfies the match criteria and that has the lowest corresponding dose and/or acquisition time may then be selected. The parameters for the selected simulated image may then be used for future image acquisition. The parameters may be those used to create the selected simulated image or those that are associated with the selected simulated image (e.g., which may be derived from the parameters used to create the selected simulated image).

In the above embodiments, multiple simulated images are first created, and the image registration module 340 is configured to register the multiple simulated images with the reference image. In other embodiments, the image registration module 340 may be configured to perform a registration after each simulated image is generated. Thus, the items 204, 206, 208 in method 200 do not need to be performed sequentially. For example, in other embodiments, a first simulated image (e.g., simulated image S10) may be created, and then the image registration module 340 is configured to register the first simulated image with the reference image. Then the apparatus 300 checks to see if the registration was performed with sufficient accuracy (e.g., meeting a prescribed accuracy requirement). If the registration was performed with sufficient accuracy, then a second simulated image (e.g., simulated image S9) with less quality than the first simulated image is created. For example, more noise may be added to create the second simulated image S9 to simulate an image as if it were acquired with less dose (compared to that corresponding with the first simulated image S10). The image registration module 340 then registers the second simulated image with the reference image. The apparatus 300 then checks to see if the registration using the second simulated image S9 was performed with sufficient accuracy. The above process is repeated with additional simulated image(s) until the registration cannot be performed to meet the prescribed accuracy. Following the example shown in FIG. 4, additional simulated images S8, S7 are created with progressively worse image qualities, and additional image registrations are performed. The registrations based on simulated images S8, S7 meet the prescribed registration criteria. Next, simulated image S6 is generated with worse quality compared to simulated image S7. After image registration is performed using the simulated image S6, the apparatus 300 determines that the registration does not meet the prescribed registration criteria. Accordingly, the apparatus 300 may then select one of the previous simulated images (previous with respect to the simulated image S6 failing the criteria), to determine a minimum acceptable dose for image generation. For example, the apparatus 300 may select the simulated image S7 that is immediately preceding the failed simulated image S6. The selected simulated image S7 was generated using an amount of noise that corresponds with a certain dose value. Thus, the minimum acceptable dose for generating future image(s) will be the dose value corresponding to the amount of noise in the selected simulated image. Alternatively, the apparatus 300 may be configured to select another simulated image (e.g., any of S8, S9, S10 in the example) to determine the minimum acceptable dose.

As shown in the above examples, items 204, 206, 208 may be performed sequentially in some embodiments, or not sequentially in other embodiments. For example, part of item 206 and part of item 208 may be performed after a part (but not all) of item 204 has been performed. In particular, a first image parameter (in item 204) may be obtained first, and then a first simulated image is generated (in item 206) using the first image parameter. A first registration is then performed (in item 208) using the first simulated image. Next, a second image parameter (in item 204) may be obtained, and then a second simulated image is generated (in item 206) using the second image parameter. A second registration is then performed (in item 208) using the second simulated image. If there are additional image parameter(s), the same goes for these other additional image parameter(s), simulated image(s), and registration(s).

In some embodiments, the image processing method 200 further includes using the image acquisition parameter to obtain a second image. For example, the image acquisition parameter may be utilized by an imaging system to obtain the second image. In one implementation, after the apparatus 300 has determined the image acquisition parameter, the apparatus 300 may then transmit the image acquisition parameter to the imaging system (e.g., through a cable or through a wireless connection). The imaging system may be an x-ray system, a fluoroscopic system, a CT system, an on-line imaging system (which may be a part of a treatment system), or any of other types of imaging system. Also, the imaging system for obtaining the second image may be a part of a treatment system, or may be used together with a treatment system. For example, the imaging system may be an on-board imager in some embodiments. In other embodiments, the imaging system may be located next to a treatment system (e.g., a radiation or proton treatment system), and may be located together with the treatment system in a same room. In other embodiments, the treatment system may be a brachytherapy system, a hyperthermia treatment system, or any of other treatment system that utilizes image-guided procedures. Also, in other embodiments, the second image may be generated during a surgery that involves use of image-guided procedure.

In some embodiments, the use of the image acquisition parameter to obtain the second image may be performed during a patient setup procedure. For example, the second image may be obtained for registration (e.g., matching) with a reference image in order to position the patient, so that the patient will be at a desired location. This may be accomplished before a treatment is performed on the patient. In other embodiments, the use of the image acquisition parameter to obtain the second image may be performed during a treatment procedure. For example, during a treatment procedure, the patient may have moved out of a desired position. In such cases, the second image may be obtained during the treatment procedure in order to reposition the patient to the desired position.

Because the parameters for image acquisition are optimized according with the technique described herein, the obtaining of the image during the patient setup and/or during treatment will result in minimal (or at least reduced) dose to the patient. The method 200 and apparatus 300 are advantageous because they provide significant improvements in image acquisition for image registration. In particular, the technique described herein provides a systematic and mathematical way to identify the most desirable image acquisition parameters for future image acquisitions, which allows image registration to be performed while reducing dose to a patient. Also, the method 200 and apparatus 300 are advantageous because they do not require use of any phantom, nor do they require use of imaging device (e.g., radiation machine) to generate multiple test images to test different image generation parameters (e.g., doses, currents, beam-on periods, etc.). Furthermore, the method 200 and apparatus 300 are advantageous because they can be applied for different registrations with different image matching requirements. For example, an image matching of a MV image may involve a different criterion (e.g., threshold) for the image matching compared to that of a kV image. As another example, an image matching of an ultrasound image may involve a different criterion (e.g., threshold) for the image matching compared to that of a x-ray image. The above method 200 and apparatus 300 allow the criterion (e.g., threshold) of the registration to be flexible and adjustable for different imaging techniques and for different imaging technologies.

In other embodiments, an optimization algorithm may be utilized to determine the parameters for future image acquisition(s). For example, instead of starting with a plurality of parameters for creating a plurality of simulated images, the apparatus 300 may start with an initial "guess" for the first simulated image. Image registration is then performed using this initial simulated image, and the quality of the registration is assessed. In one implementation, in the optimization process, the quality of registration would be a constraint as it would have to reach a minimal acceptable level, while the cost function would be a function of dose, imaging time, number of projection images, or any combination of the foregoing. Also, in some embodiments, the parameters to be optimized may include electrical current (for image acquisition), time of beam-on, number of projections, projection angles, or any combination of the foregoing. Also, in some embodiments, the results from iteration i in the optimization process may be used to generate new parameters for iteration i+1. The parameters may then be used to determine a second simulated image (for iteration i+1), and the above technique is repeated until optimal parameters are determined. In some embodiments, the optimization process may utilize a convex cost function. Also, in some embodiments, the optimization process may utilize conjugate gradient method, gradient descent method, etc.

Specialized Processing System

Figure 5:
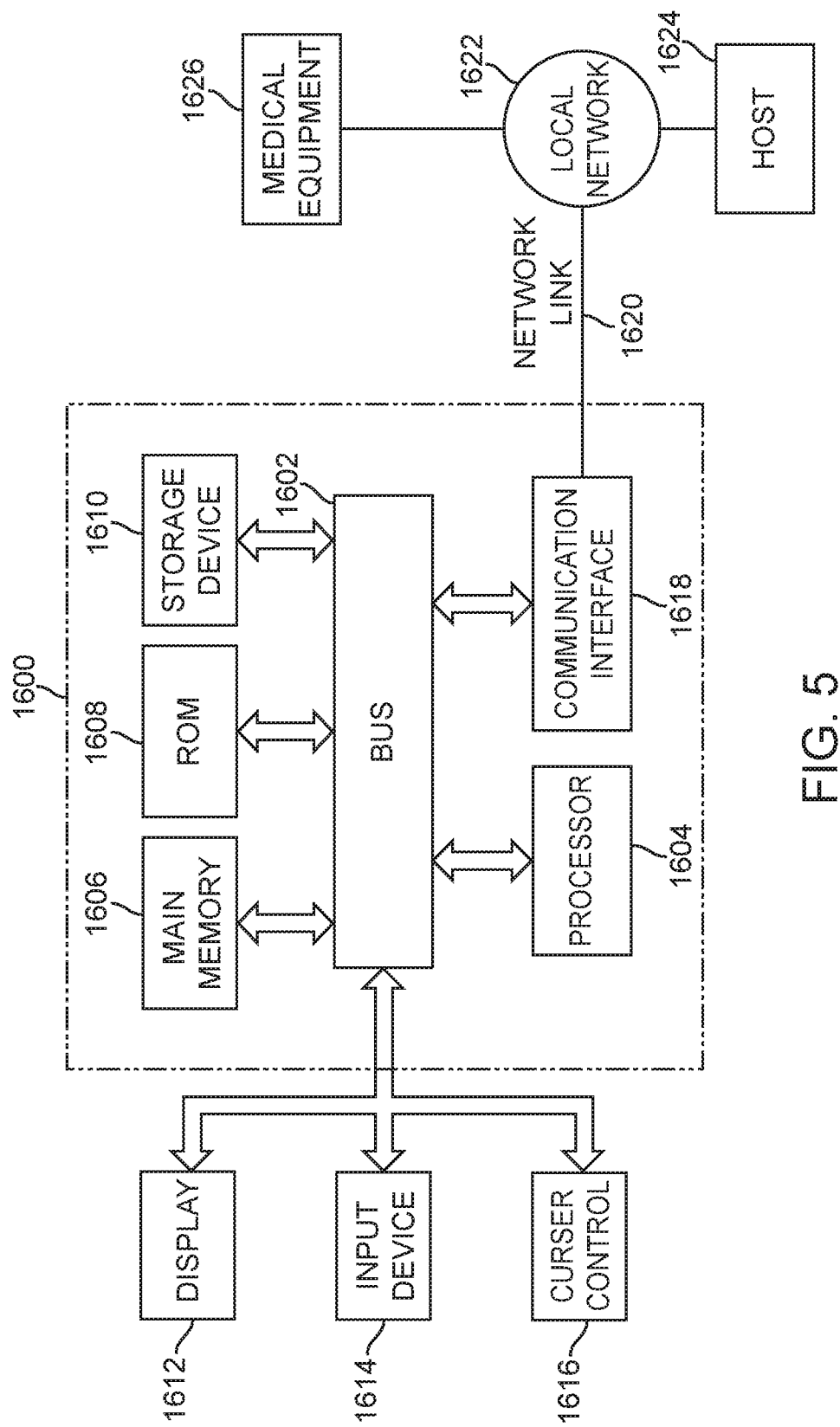
FIG. 5 illustrates a computer system with which embodiments described herein may be implemented in accordance with some embodiments.

FIG. 5 is a block diagram illustrating an embodiment of a specialized processing system 1600 that can be used to implement various embodiments described herein. For example, the processing system 1600 may be configured to implement the method of FIG. 2 in accordance with some embodiments. Also, in some embodiments, the processing system 1600 may be used to implement the apparatus 300 of FIG. 3 and/or the processing unit 54 of FIG. 1. The processing system 1600 may be used to implement the apparatus 300 of FIG. 3, or any of the components therein. The processing system 1600 may also be an example of any processor described herein.

Processing system 1600 includes a bus 1602 or other communication mechanism for communicating information, and a processor 1604 coupled with the bus 1602 for processing information. The processor system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The processor system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The processor system 1600 may be coupled via the bus 1602 to a display 167, such as a cathode ray tube (CRT), for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the processor system 1600 can be used to perform various functions described herein. According to some embodiments, such use is provided by processor system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another processor-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "processor-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. A non-volatile medium may be considered an example of non-transitory medium. Volatile media includes dynamic memory, such as the main memory 1606. A volatile medium may be considered an example of non-transitory medium. Transmission media includes coaxial cables, copper wire and fiber optics, including the wires that comprise the bus 1602. Transmission media can also take the form of acoustic or light waves, such as those generated during radio wave and infrared data communications.

Common forms of processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a processor can read.

Various forms of processor-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a telephone line using a modem. A modem local to the processing system 1600 can receive the data on the telephone line and use an infrared transmitter to convert the data to an infrared signal. An infrared detector coupled to the bus 1602 can receive the data carried in the infrared signal and place the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The processing system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the processing system 1600, are exemplary forms of carrier waves transporting the information. The processing system 1600 can send messages and receive data, including program code, through the network(s), the network link 1620, and the communication interface 1618.

It should be noted that, as used in this specification, the term "image" is not necessarily limited to image that is displayed, and may refer to image that is not displayed as well. For example, in some embodiments, any of the images described herein may be stored in a non-transitory medium as image data.

Also, the term "processor" may include one or more processing units, and may refer to any device that is capable of performing mathematical computation implemented using hardware and/or software. The term "processor" may also refer to software stored in a non-transitory medium in other embodiments. Further, in any of the embodiments described herein, instead of using the processor 54 to perform the various functions described, a separate processor may be used.

Although particular embodiments have been shown and described, it will be understood that they are not intended to limit the claimed inventions, and it will be obvious to those skilled in the art that various changes and modifications may be made without departing from the spirit and scope of the claimed inventions. The specification and drawings are, accordingly, to be regarded in an illustrative rather than restrictive sense. The claimed inventions are intended to cover alternatives, modifications, and equivalents.

What is claimed:

1. An apparatus, comprising:
one or more input for electronically obtaining a first image and for obtaining a plurality of image parameters that includes at least a first image parameter and a second image parameter;
a simulated image generator, and an image registration module coupled downstream with respect to the simulated image generator, wherein the simulated image generator and the image registration module are implemented using a processor;
wherein the simulated image generator is configured for electronically generating a plurality of simulated images based on the first image and the plurality of image parameters, the plurality of simulated images having at least a first simulated image computed based on the first image parameter, and a second simulated image computed based on the second image parameter, wherein the first simulated image has a first image quality, the second simulated image has a second image quality, and the first image quality is different from the second image quality;
wherein the image registration module is configured for signal processing to electronically perform a plurality of image registrations using the simulated images, and for generating registration data representing results from the act of performing the plurality of image registrations;
wherein the apparatus is configured to provide image acquisition parameter via a communication interface based at least on one or more of the registration data, and wherein in an imaging system that is configured to perform image acquisition, the image acquisition parameter controls or affects a manner in which the image acquisition is performed by the imaging system.

2. The apparatus of claim 1, wherein the first image comprises a CT image.

3. The apparatus of claim 1, wherein the first image parameter corresponds with a first dose, and the second image parameter corresponds with a second dose that is different from the first dose.

4. The apparatus of claim 1, wherein the first image parameter corresponds with a first current value for image acquisition, and the second image parameter corresponds with a second current value that is different from the first current value.

5. The apparatus of claim 1, wherein the first image parameter corresponds with a first period for image acquisition, and the second image parameter corresponds with a second period that is different from the first period.

6. The apparatus of claim 1, wherein the first image parameter corresponds with a first number of projection images, and the second image parameter corresponds with a second number of projection images that is different from the first number of projection images.

7. The apparatus of claim 1, wherein the image registration module is configured to register the first simulated image with a reference image and to register the second simulated image with the reference image.

8. The apparatus of claim 7, wherein the reference image comprises the first image or a portion of the first image.

9. The apparatus of claim 7, wherein the reference image is derived from the first image.

10. The apparatus of claim 1, wherein the registration data comprises a plurality of values representing how well the respective simulated images match with a reference image.

11. The apparatus of claim 10, wherein the values comprise cross correlation values.

12. The apparatus of claim 10, wherein the values comprise mutual information.

13. The apparatus of claim 1, wherein the image registration module is configured to use a rigid registration algorithm to perform the plurality of image registrations.

14. The apparatus of claim 1, wherein the image registration module is configured to use a deformable registration algorithm to perform the plurality of image registrations.

15. The apparatus of claim 1, wherein the image registration module is configured to perform the plurality of image registrations based on a match criteria.

16. The apparatus of claim 1, wherein the image registration module is configured to perform the plurality of image registrations based on an input from a user.

17. The apparatus of claim 16, wherein the input comprises a region-of-interest.

18. The apparatus of claim 16, wherein the input comprises an identification of a structure.

19. The apparatus of claim 1, wherein the image acquisition parameter corresponds with one of the simulated images that satisfies a cut-off criteria, and has a lowest corresponding dose.

20. The apparatus of claim 1, wherein the image acquisition parameter is for obtaining a second image.

21. The apparatus of claim 20, wherein the image acquisition parameter is for obtaining the second image during a patient setup procedure.

22. An image processing method, comprising:
electronically obtaining a first image;
electronically obtaining a plurality of image parameters that includes at least a first image parameter and a second image parameter;
electronically generating, using a simulated image generator, a plurality of simulated images based on the first image and the plurality of image parameters, the plurality of simulated images having at least a first simulated image computed based on the first image parameter, and a second simulated image computed based on the second image parameter, wherein the first simulated image has a first image quality, the second simulated image has a second image quality, and the first image quality is different from the second image quality;
signal processing by an image registration module, to electronically perform a plurality of image registrations using the simulated images, and to generate registration data representing results from the act of performing the plurality of image registrations; and providing, via a communication interface, image acquisition parameter based at least on one or more of the registration data;
wherein the image registration module is coupled downstream with respect to the simulated image generator, and wherein the simulated image generator and the image registration module are implemented using a processor; and
wherein in an imaging system that is configured to perform image acquisition, the image acquisition parameter controls or affects a manner in which the image acquisition is performed by the imaging system.

23. The image processing method of claim 22, wherein the first image comprises a CT image.

24. The image processing method of claim 22, wherein the first image parameter corresponds with a first dose, and the second image parameter corresponds with a second dose that is different from the first dose.

25. The image processing method of claim 22, wherein the first image parameter corresponds with a first current value for image acquisition, and the second image parameter corresponds with a second current value that is different from the first current value.

26. The image processing method of claim 22, wherein the first image parameter corresponds with a first period for image acquisition, and the second image parameter corresponds with a second period that is different from the first period.

27. The image processing method of claim 22, wherein the first image parameter corresponds with a first number of projection images, and the second image parameter corresponds with a second number of projection images that is different from the first number of projection images.

28. The image processing method of claim 22, wherein the act of performing the plurality of image registrations using the simulated images comprises registering the first simulated image with a reference image and registering the second simulated image with the reference image.

29. The image processing method of claim 28, wherein the reference image comprises the first image or a portion of the first image.

30. The image processing method of claim 28, wherein the reference image is derived from the first image.

31. The image processing method of claim 22, wherein the registration data comprises a plurality of values representing how well the respective simulated images match with a reference image.

32. The image processing method of claim 31, wherein the values comprise cross correlation values.

33. The image processing method of claim 31, wherein the values comprise mutual information.

34. The image processing method of claim 22, wherein the act of performing the plurality of image registrations comprises using a rigid registration algorithm.

35. The image processing method of claim 22, wherein the act of performing the plurality of image registrations comprises using a deformable registration algorithm.

36. The image processing method of claim 22, further comprising obtaining match criteria, wherein the act of performing the plurality of image registrations is performed based on the match criteria.

37. The image processing method of claim 22, further comprising obtaining an input from a user, wherein the act of performing the plurality of image registrations is performed based on the input from the user.

38. The image processing method of claim 37, wherein the input comprises a region-of-interest.

39. The image processing method of claim 37, wherein the input comprises an identification of a structure.

40. The image processing method of claim 22, wherein the image acquisition parameter corresponds with one of the simulated images that satisfies a cut-off criteria, and has a lowest corresponding dose.

41. The image processing method of claim 22, further comprising using the image acquisition parameter to obtain a second image.

42. The image processing method of claim 41, wherein the second image is obtained during a patient setup procedure.

43. A product having a non-transitory medium storing instructions, an execution of which causes a processing unit to perform a method, the method comprising:
   electronically, obtaining a first image;
   electronically, obtaining a plurality of image parameters that includes at least a first image parameter and a second image parameter;
   electronically generating, using a simulated image generator, a plurality of simulated images based on the first image and the plurality of image parameters, the plurality of simulated images having at least a first simulated image computed based on the first image parameter, and a second simulated image computed based on the second image parameter, wherein the first simulated image has a first image quality, the second simulated image has a second image quality, and the first image quality is different from the second image quality;
   signal processing by an image registration module, to perform a plurality of image registrations using the simulated images, and to generate registration data representing results from the act of performing the plurality of image registrations; and
   providing, via a communication interface, image acquisition parameter based at least on one or more of the registration data;
   wherein the image registration module is coupled downstream with respect to the simulated image generator, and wherein the simulated image generator and the image registration module are implemented using a processor; and
   wherein in an imaging system that is configured to perform image acquisition, the image acquisition parameter controls or affects a manner in which the image acquisition is performed by the imaging system.

\* \* \* \* \*